United States Patent [19]

Su

[11] Patent Number: 5,066,804
[45] Date of Patent: Nov. 19, 1991

[54] PREPARATION OF ALKYL MORPHOLINONES

[75] Inventor: Wei-Yang Su, Austin, Tex.

[73] Assignee: Texaco Chemical Company, White Plains, N.Y.

[21] Appl. No.: 596,642

[22] Filed: Oct. 12, 1990

[51] Int. Cl.$^5$ ............................................ C07D 265/32
[52] U.S. Cl. .................................................... 544/173
[58] Field of Search ........................................ 544/173

[56] References Cited

PUBLICATIONS

Laurent et al., Bull. Soc. Chim. Fr., 83 (1978) II, pp. 83–88.

*Primary Examiner*—Robert W. Ramsuer
*Attorney, Agent, or Firm*—Jack H. Park; Kenneth R. Priem; Carl G. Ries

[57] ABSTRACT

A 4-alkyl-2-morpholinone is prepared by reacting glyoxal with a $C_1$–$C_{18}$ N-alkylmonoethanolamine in solution in a solvent that azeotropes with water at a temperature of about $-10°$ to $20°$ C. for about 1 to 5 hours and by then heating the reaction mixture to a temperature of at least about $110°$ C. to remove an azeotrope of water and solvent from the mixture to thereby substantially selectively convert the $C_1$–$C_{18}$ N-alkylmonoethanolamine to the corresponding 4-alkyl-2-morpholinone.

6 Claims, No Drawings

PREPARATION OF ALKYL MORPHOLINONES

BACKGROUND OF THE INVENTION

1. Technical Field of the Invention

This invention relates to a process for preparing 4-alkyl-2-morpholinones from glyoxal and N-alkylmonoethanolamines. More particularly, this invention relates to a process for the reaction of glyoxal with a N-alkylmonoethanolamine in solution in toluene in order to prepare the corresponding 4-alkyl-2-morpholinone in good yield and selectivity.

The 4-alkyl-2-morpholinones are useful as intermediates for the preparation of surfactants as shown, for example, in U.S. Pat. No. 4,228,096 and are also useful as solvents.

2. Prior Art

Laurent and Bearn in an article entitled "The Reactions of Glyoxal with Amino-Alcohols" (*Bull. Soc. Chim. Fr.* 83 (1978 II), pp. 83-88) disclose the reaction of glyoxal with N-alkylaminoethanols. They report that they obtained about a 40% yield of N,N'-disubstituted-3,3'-dioxazolidines instead of the expected 2-formyl oxazolidine because of the concommitment formation of N-alkyl-2-morpholones, N-alkyl, N-(2-hydroxyethyl)acetic acids and N-alkyl-2,3-epoxy morpholines.

Schultz et al. U.S. Pat. No. 3,073,822 is directed to a process for the preparation of 4-substituted-2-morpholones by the hydrogenation of N-substituted-dialkanolamines in vapor phase in the presence of a catalyst.

Haas U.S. Pat. No. 4,695,630 is directed to a process for the preparation of polycyclic acetals by the reaction of 2,3-dihydroxydioxane with a 1,2-amino alcohol in an inert solvent.

Jankowski and Berse in a paper entitled "Preparation of Novel Derivatives of Morpholone-2" (*Canadian Journal of Chemistry*, Vol. 46, 1968, pp. 1939-1942) disclose a process wherein an amine acid is reacted with an epoxide to give a morpholone-2 compound.

Vieles and Galsomias in a paper published in the Bulletin of the Chemical Society of France (*Bull. Soc. Chim. Fr.*, 1970, pp. 2529-2534) disclose a process wherein amino alcohols are reacted with halogen esters.

In an article entitled "High-Yield Syntheses of N-(2-Hydroxyethyl)-N-alkylglycine Derivatives by Reaction of Ethanolamines with Glyoxal", *Synthesis*, 927-929 (1987), Farfan et al. disclose the reaction of N-alkylethanolamines with glyoxal to provide high yields of N-(2-hydroxyethyl)-N-alkylglycine derivatives by conducting the reaction at an elevated temperature of about 70° C.

SUMMARY OF THE INVENTION

The present invention is directed to a method for the preparation of 4-alkyl-2-morpholinones from glyoxal and a N-alkylmonoethanolamine.

It has been discovered in accordance with the present invention that a significant improvement in yield and selectivity can be obtained if the N-alkylmonoethanolamine is reacted with glyoxal in solution in a solvent that will form an azeotrope with water (e.g., toluene) at a temperature of −10° to about 20° C. for about 1 to 5 hours followed by heating of the reaction mixture to a reflux temperature such as a temperature of about 110° C. in order to remove water from the reaction mixture as an azeotrope of water with toluene. When this procedure is followed, the formation of reaction by-products is minimized.

DESCRIPTION OF THE PREFERRED EMBODIMENT

The starting materials for the present invention are glyoxal, an N-alkyl-monoethanolamines wherein the alkyl group contains 1 to 18 carbon atoms. Toluene is also present as a solvent.

Representative N-alkylmonoethanolamines that can be used as starting materials for the process of the present invention include compounds such as N-methyl-monoethanolamine, N-ethyl-monoethanolamine, N-isopropyl-monoethanolamine, N-dodecyl-monoethanolamine, N-hexadecyl-monoethanolamine, etc.

The reaction conditions to be used in conducting the process of the present invention include a temperature within the range of about −10° to about 20° C. It has been unexpectedly discovered that if higher temperatures are used the formation of by-products is increased. More preferably, the reaction will be conducted at a temperature within the range of −10° to about 10° C.

The reaction is preferably conducted for a period of time within the range of about 1 to about 5 hours, such as a reaction time of about 1 to 2 hours.

At the end of the reaction, the reaction mixture will comprise a toluene solution of the desired 4-alkyl-2-morpholinone precursor and water in toluene.

It has been further discovered in accordance with the present invention that it is important to remove the water from the reaction mixture by azeotropic distillation with a methyl, dimethyl or ethyl benzene solvent in order to inhibit the formation of additional by-products.

Preferably, about equimolar amounts of glyoxal and the N-alkylmonoethanolamine are used. If desired, a slight excess of either of the reactants may be employed in order to ensure that the reaction goes to completion.

The reaction between the glyoxal and the N-alkylmonoethanolamine is a noncatalytic reaction.

In accordance with the present invention, the reaction is conducted in solution in a methyl, dimethyl or ethyl benzene solvent (i.e., toluene, a xylene or ethylbenzene). Toluene is preferred. Toluene is a good solvent for the 4-alkyl-2-ethanolamine reactant as well as for the 4-alkyl-2-morpholinone reaction product.

At the end of the reaction, the reaction mixture should be heated to reflux temperature, such as the temperature of 110° C., in order to remove all of the by-product water by azeotropic distillation. Accordingly, the amount of solvent should be at least about 1 mole per mole of N-alkylmonoethanolamine. Preferably, an excess of solvent is used, so that the reaction mixture will preferably contain from about 1 to about 5 moles of solvent per mole of 4-alkyl-diethanolamine.

After the removal of the water and toluene, the desired 4-alkyl-2-morpholinone can be recovered by simple distillation from the reaction mixture.

SPECIFIC EXAMPLES

The invention will be further illustrated by the following specific examples which are given by way of illustration and not as limitations on the scope of the invention.

Example 1 - Preparation of 4-Methyl-2-Morpholinone (6621-7)

To a 500-ml three-necked flask equipped with a stirrer, thermometer, and addition funnel was added 145 g of glyoxal solution (40% aqueous solution, 1 mol) in 100 g of toluene. Cool the reaction flask. Then a solution of 75.1 g of N-methylmonoethanolamine (1 mol) in 50 g of toluene was added at the temperature 5° C.–10° C. The reaction mixture was stirred for additional two hours at temperature below room temperature and then heated to reflux to azeotrope out water. The product was distilled to give 100.9 g of 4-methyl-2-morpholinone (88% yield).

Example 2 (6621-10)

The procedure of Example 2 was followed except that the reaction was carried out at about 25° C. initially. About 91 g of 4-methyl-2-morpholinone was obtained (79% yield). This example demonstrated that lower yield was obtained when the reaction was carried out at relative higher temperature.

Example 3 - Preparation of 4-Ethyl-2-Morpholinone (6621-11)

The procedure of Example 2 was followed except that N-ethylmonoethanolamine (89.1 g, 1 mol) was used. About 112.6 g of 4-ethyl-2-morpholinone was obtained (87% yield).

Example 4 - Preparation of 4-Isopropyl-2-Morpholinone (6621-12)

The procedure of Example 1 was followed except that N-isopropylmonoethanolamine (103.1 g, 1 mol) was used. About 133.4 g of 4-isopropyl-2-morpholinone was obtained (93% yield).

Example 5 (6621-13)

The procedure of Example 1 was followed except that tetrahydrofuran was used as solvent and the product was distilled without azeotroping out water. About 90.4 g of 4-isopropyl-2-morpholinone was obtained (63% yield). This example along with the Example 4 demonstrates that using solvent to azeotrope out water give a better yield of the desired product.

Having thus described my invention, what is claimed is:

1. A method for the preparation of a 4-alkyl-2-morpholinone which comprises reacting glyoxal with a N-alkyl monoethanolamine at a temperature of about −10° to 20° C. for about 1 to 5 hours in solution in a solvent that will form an azeotrope with water selected from the group consisting of toluene, xylene and ethyl benzene and then heating the reaction mixture to a temperature of at least about 110° C. to remove an azeotrope of water and solvent from the mixture to thereby substantially selectively convert the N-alkylmonoethanolamine to the corresponding 4-alkyl-2-morpholinone, and recovering the 4-alkyl-2-morpholinone, the alkyl group of said N-alkyl monoethanolamine containing 1 to 18 carbon atoms.

2. A method as in claim 1 wherein the solvent is toluene.

3. A method as in claim 2 wherein the reaction is conducted at a temperature of about −10° to about 10° C.

4. A method as in claim 3 wherein the N-alkylmonoethanolamine is N-methyl-monoethanolamine.

5. A method as in claim 3 wherein the N-alkylmonoethanolamine is N-ethyl-monoethanolamine.

6. A method as in claim 3 wherein the N-alkylmonoethanolamine is N-isopropyl-monoethanolamine.

* * * * *